(12) United States Patent
Shekhawat et al.

(10) Patent No.: US 7,157,897 B2
(45) Date of Patent: Jan. 2, 2007

(54) METHOD AND SYSTEM FOR ELECTRONIC DETECTION OF MECHANICAL PERTURBATIONS USING BIMOS READOUTS

(75) Inventors: Gajendra Shekhawat, Arlington Heights, IL (US); Vinayak P. Dravid, Glenview, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/996,274

(22) Filed: Nov. 23, 2004

(65) Prior Publication Data

US 2005/0151530 A1 Jul. 14, 2005

Related U.S. Application Data

(60) Provisional application No. 60/524,994, filed on Nov. 25, 2003.

(51) Int. Cl.
*G01N 27/00* (2006.01)
*G01B 5/28* (2006.01)

(52) U.S. Cl. .................. 324/71.1; 324/71.4; 73/105; 73/580

(58) Field of Classification Search ........... 324/504.15, 324/71.6
See application file for complete search history.

(56) References Cited

U.S. PATENT DOCUMENTS

| 5,458,222 | A | * | 10/1995 | Pla et al. ................. 188/378 |
| 5,742,377 | A |   | 4/1998  | Minne et al. |
| 5,930,666 | A | * | 7/1999  | Pankove ................... 438/615 |
| 5,953,603 | A | * | 9/1999  | Kim ......................... 438/202 |
| 6,203,983 | B1 | * | 3/2001 | Quate et al. ................ 435/6 |
| 6,237,399 | B1 | * | 5/2001 | Shivaram et al. ............. 73/105 |
| 6,613,601 | B1 | * | 9/2003 | Krauss et al. ................. 438/52 |
| 6,680,788 | B1 | * | 1/2004 | Roberson et al. ........... 359/210 |
| 6,713,389 | B1 | * | 3/2004 | Speakman ................... 438/674 |
| 6,777,529 | B1 | * | 8/2004 | Ong et al. ................... 528/373 |
| 6,906,450 | B1 | * | 6/2005 | Tamayo De Miguel et al. . 310/317 |

OTHER PUBLICATIONS

IBM Press Release, http://domino.research.ibm.com/comm/pr.nsf/pages/news.20020520_nanotubes.html, May 20, 2002.*
G. Miller, W.C. Inkret, M.E. Schillaci, H.F. Martz, T.T. Little, Health Physics, vol. 78 (2000) 598.
N. Iznaga, G. Nunez, J. Solozabal, A. Morales, E. Artaza, R. Rubio, E. Cardenas, Computer Methods and Programs in Biomedicine, vol. 47 (1995) 1678.
W. Gopel, Chemical imaging. I. Concepts and visions for electronic and bioelectronics noises, sensors and actuators B, B52 (1998) 125.
C. Nicolini, Thin solid films, vol. 284-285 (1996) 1; O.H. Willemsen, M.M.E. Snel, A. Cambi, J. Greve, B.G. Gooth, C.G. Figdor, Biophysical Journal, vol. 79 (2000) 3276.

(Continued)

*Primary Examiner*—Andrew H. Hirshfeld
*Assistant Examiner*—John Zhu
(74) *Attorney, Agent, or Firm*—McAndrews, Held & Malloy, Ltd.

(57) ABSTRACT

A sensor for detecting mechanical perturbations represented by a change in an electrical signal includes a structure such as a cantilever, membrane, etc. and a field effect transistor such as a MOSFET embedded in the structure. The drain current of the embedded transistor changes with mechanical perturbations in the structure caused, for example, by a bio-chemical interaction being sensed. A scanning probe microscope utilizes the embedded MOSFET with a BiMOS actuator.

3 Claims, 11 Drawing Sheets

OTHER PUBLICATIONS

M. Gomez-Lopez, J.A. Preece, J.F. Stoddart, Nanotechnology, vol. 7 (1996) 183.

M. Bras, J. Cloarec, F. Bessueille, E. Souteyrand, J. Martin, Journ. of Fluores., vol. 10 (2000) 247.

J. Fritz, M.K. Baller, H.P. Lang, H. Rothuizen, P. Vettiger, E. Meyer, H.J. Guntherodt, Ch. Gerber J.K. Gimzewski, Translating biomolecular recognition into nanomechanics, Science 288: 316-318 (2000).

R. McKendry, J.Y. Zhang, Y. Arntz, T. Strunz, M. Hegner, H.P. Lang, M.K. Baller, U. Certa, E. Meyer, H.J. Guntherodt, C. Gerber, Multiple label-free biodetection and quantitive DNA-binding assays on a nanomechanical cantilever array, PNAS 99: 9783-9788 (2002).

Y. Arntz, J.D. Seelig, H.P. Lang, J. Zhang, P. Hunziker, J.P. Ramseyer, E. Meyer, M. Hegner, C. Gerber, Label-free protein assay based on a nanomechanical cantilever array, Nanotechnology 14: 86-90 (2003).

R. Berger, E. Delmarche, H.P. Lang, Ch. Gerber, J.K. Gimzewski, E. Meyer, H.J. Guntherodt, Surface stress I the self assembly of alkanethiols on gold, Science, vol. 276 (1997) 2021.

S.J. O'Shea, M.E. Welland, T.A. Brunt, A. Ramadan, T. Rayment, Atomic force microscopy stress sensors for studies in liquids, J. Vac. Si. Technol., vol. B14 (1996) 1383.

M. Tortonese, R.C. Barrett, C.F. Quate, Atomic resolution with an atomic force microscope using piezoresistive detection, Appl. Phys. Letters, vol. 62 (1993) 834.

A. Boisen, J. Thaysen, H. Jensenius and O. Hansen, Environmental sensors based on micromachined cantilevers with integrated read-out, Ultramicroscopy 82 (2000) 11-16.

S. Minne, G. Yaralioglu, S. Manalis, J.A. Adams, C. Quate, Appl. Phys. Lett., vol. 72 (1998) 2340.

S.C. Minne, S.R. Manalis, C.F. Quate, Integrated piezo-resistive and piezo-actuator based parallel scanning probe microscope, Appl. Phys. Letts., vol. 67 (1995) 3918.

IBM Creates World's Highest Performing Nanotube Transistors, IBM Press Release (May 20, 2002).

International Search Report (PCT/US2004/39685).

* cited by examiner

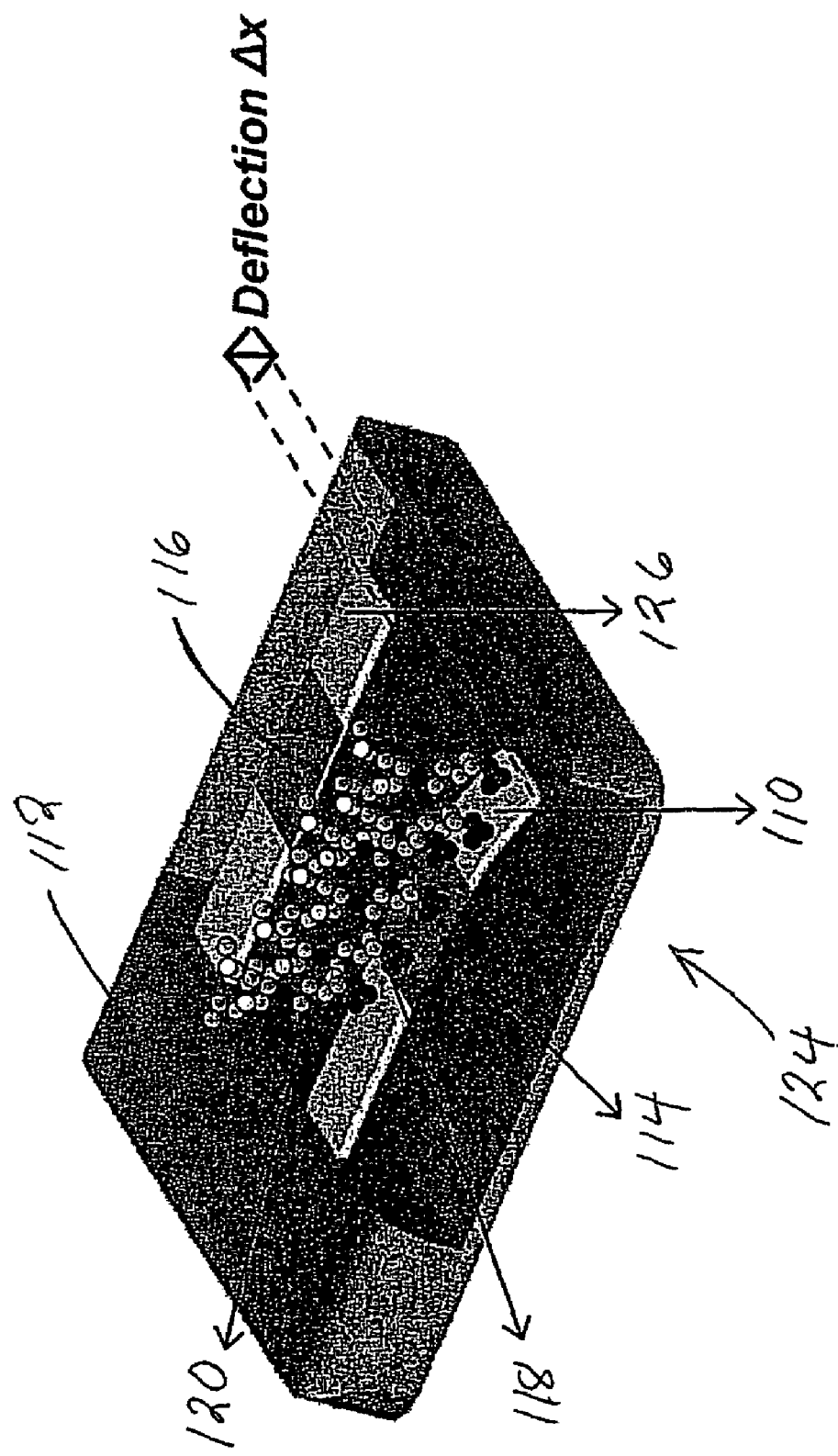

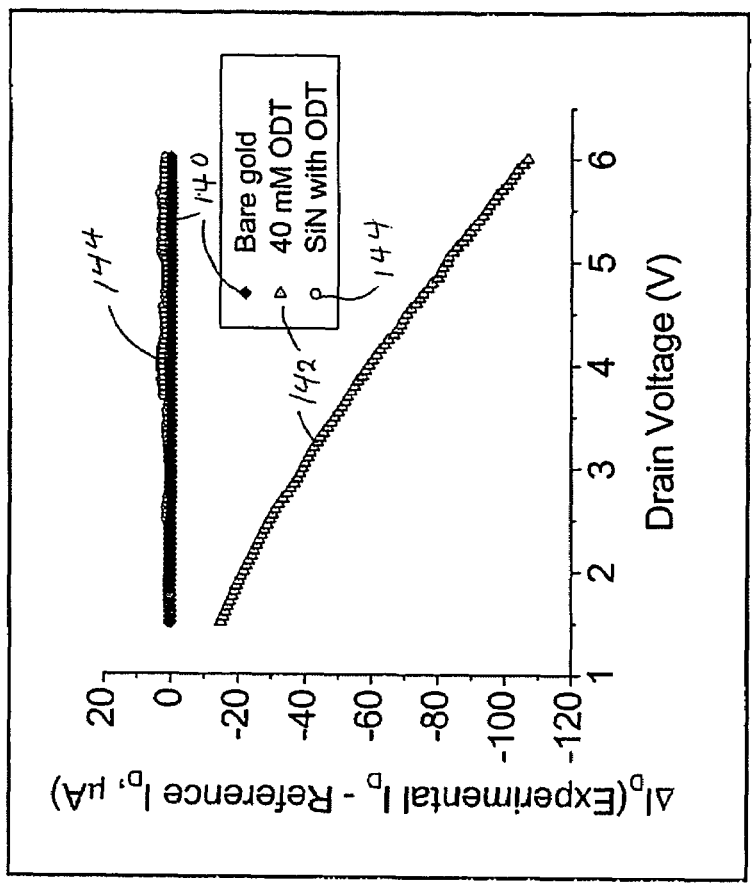
FIG. 12 — Change in drain current vs. drain voltage at Gv=1.0 V
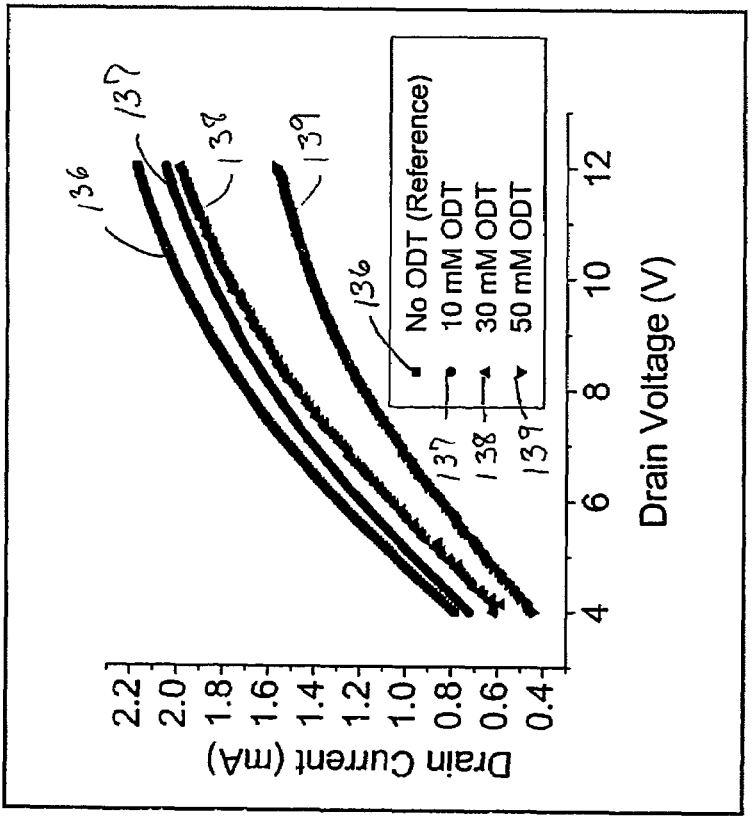
FIG. 11 — Drain current vs. drain voltage for different ODT concentrations at Gv=1.5 V.

⇧ Change in drain current vs. drain voltage at Gv=1.0 V for 40 nM target ssDNA.

⇧ Drain current vs. time for 40 nM target ssDNA hybridization at Gv=1.0 V and Dv=6.0 V. Drain current decreased with hybridization time and reached saturation in ~30 min.

Drain current vs. time for streptavidin and 50nM biotin binding at Gv=1.0 V and 3 different drain voltages.

Time-dependent drain current vs. drain voltage measurement for streptavidin and 50 nM biotin binding at Gv= 1.0 V.

Drain current vs. time for 3 different drain voltages.

Drain current vs. drain voltage at Gv=1.0 V. Drain current decreased with antigen (0.1 mg/ml) antibody (0.1 mg/ml) binding

METHOD AND SYSTEM FOR ELECTRONIC DETECTION OF MECHANICAL PERTURBATIONS USING BIMOS READOUTS

CROSS-REFERENCE TO RELATED APPLICATIONS

The present application claims the priority of provisional patent application Ser. No. 60/524,994 filed Nov. 25, 2003. That application is hereby incorporated herein by reference.

STATEMENT REGARDING FEDERALLY SPONSORED RESEARCH OR DEVELOPMENT

This work was supported by the National Science Foundation (NSF) awards: # NSEC-EEC-0118025, and ECS-0330410, and Air Force Office of Scientific Research (AFOSR)-MURI # F49620-00-1-0283.

BACKGROUND OF THE INVENTION

Most biosensors and chemical sensors rely on specific molecular recognition events. See for example, G. Miller, W. C. Inkret, M. E. Schillaci, H. F. Martz, T. T. Little, Health Physics, Volume 78 (2000) 598; N. Iznaga, G. Nunez, J. Solozabal, A. Morales, E. Artaza, R. Rubio, E. Cardenas, Computer Methods and Programs in Biomedicine, Volume 47 (1995) 167; W. Gopel, Chemical imaging. 1. Concepts and visions for electronic and bioelectronics noises, sensors and actuators B, B52 (1998) 125; C. Nicolini, Thin solid films, Volume 284–285 (1996) 1; O. H. Willemsen, M. M. E. Snel, A. Cambi, J. Greve, B. G. Gooth, C. G. Figdor, Biophysical Journal, Volume 79 (2000) 3276 and M. Gomez-Lopez, J. A. Preece, J. F. Stoddart, Nanotechnology, Volume 7 (1996) 183. Specific molecular recognition events may be an antibody-antigen, DN-DNA, or other ligand-receptor interactions. These recognition events are most commonly detected indirectly by various labeling techniques including radioactivity, enzymatic activity, visible markers, or fluorescent labels. See for example, M. Bras, J. Cloarec, F. Bessueille, E. Souteyrand, J. Martin, Journ. of Fluores., Vol. 10 (2000) 247. However, such techniques can be time consuming and often require relatively large, expensive instrumentation. Thus, there is a need for label free and continuous nanobiosensors for monitoring of bioaffinity interactions that can be easily integrated in array architecture on a CMOS chip. However, for most applications, arrays of currently available biosensors possess insufficient performance either due to large size, poor cross sensitivity, or long response times. Also, the majority of currently available biosensors are not compatible with complete CMOS Integration. Either the operation parameters of the biosensor are incompatible with CMOS, e.g. radioactive or fluorescence labeling, or the biosensor materials cannot be integrated within a CMOS process.

Recent efforts have focused on the development of cantilever-based sensors for the detection and transduction of chemical and biological processes. See for example, J. Fritz, M. K. Baller, H. P. Lang, H. Rothuizen, P. Vettiger, E. Meyer, H. J. Guntherodt, Ch. Gerber J. K. Gimzewski, Translating biomolecular recognition into nanomechanics, Science 288: 316–318 (2000); R. McKendry, J. Y. Zhang, Y. Amtz, T. Strunz, M. Hegner, H. P. Lang, M. K. Baller, U. Certa, E. Meyer, H. J. Guntherodt, C. Gerber, Multiple label-free biodetection and quantitive DNA-binding assays on a nano-mechanical cantilever array, PNAS 99: 9783–9788 (2002); Y. Amtz, J. D. Seelig, H. P. Lang, J. Zhang, P. Hunziker, J. P. Ramseyer, E. Meyer, M. Hegner, C. Gerber, Label-free protein assay based on a nanomechanical cantilever array, Nanotechnology 14: 86–90 (2003); R. Berger, E. Delmarche, H. P. Lang, Ch. Gerber, J. K. Gimzewski, E. Meyer, H. J. Guntherodt, Surface stress I the self assembly of alkanethiols on gold, Science, Vol. 276 (1997) 2021; S. J. O'Shea, M. E. Welland, T. A. Brunt, A. Ramadan, T. Rayment, Atomic force microscopy stress sensors for studies in liquids, J. Vac. Si. Technol., Volume B14 (1996) 1383; M. Tortonese, R. C. Barrett, C. F. Quate, Atomic resolution with an atomic force microscope using piezoresistive detection, Appl. Phys. Letters, Volume 62 (1993) 834. Through various physical or chemical mechanisms, biological and chemical processes may induce nanomechanical motion in a microfabricated Si cantilever array. For example, asymmetric (one-side only) molecular adsorption induces incremental surface stress, which produces a nanoscale deflection in high-Q ($>10^4$) cantilever systems. Because of their low mass and high Q-factors, these miniaturized sensors show fast response times, high sensitivity, and are suitable for mass production using standard IC fabrication.

In order to monitor cantilever deflection, an optical detector is employed to detect the reflection of a laser off of the tip of the cantilever. This technique offers excellent sensitivity to molecular adsorption. Moreover, well-established techniques of surface functionalization (chemical and biomolecular) provide a contrast mechanism for molecule-specific adsorption. However, the required optical system to measure cantilever deflection limits application to 10 s or 100 s of cantilevers and reduces its applicability to large (1000 s to 10,000 s) arrays. Optical-based techniques also require a relatively large amount of power (i.e. a dedicated lasers/detectors) and are less able to be miniaturized.

An electronic detection method for biomolecules using symmetrical wheatstone bridge configuration (piezo-resistive detection) is described in A. Boisen, J. Thaysen, H. Jensenius and O. Hansen, Environmental sensors based on micromachined cantilevers with integrated read-out, Ultra-microscopy 82 (2000) 11–16. In this design a full wheatstone bridge was placed symmetrically on a chip. Two adjacent cantilevers comprise two of the bridge resistors. The second two resistors are placed on the substrate (via doping by Ion-implantation). This design enables differential measurements where the signals from the two cantilevers are subtracted. The relative resistance change of the piezo-resistor ($\Delta R/R$) will be detected as an output voltage ($V_o$) from the wheatstone bridge with a supply voltage (V). The output voltage can be written as $V_o = \frac{1}{4} V (\Delta R/R)$. A differential amplifier will amplify the differential signal to improve the sensitivity of the cantilevers. Unfortunately, this detection method has a number of technological problems. One problem relates to non-linearities in the measurements. Another problem is serious low frequency noise. The cantilever bends by a few nanometers upon adsorption induced surface stress, so that even small noise issues cripple the validity of the measurements. further problem is concerned with the difficulty of integration on a CMOS platform, which is required for miniaturization and on chip signal transmission and detection.

Utilizing combined electrical sensing and actuation of Si micro-cantilevers has been demonstrated in atomic force microscope imaging of materials such as graphite. See for example, S. Minne, G. Yaralioglu, S. Manalis, J. A. Adams, C. Quate, Appl. Phys. Lett., Vol. 72 (1998) 2340; S. C. Minne, S. R. Manalis, C. F. Quate, Integrated piezo-resistive and piezo-actuator based parallel scanning probe microscope, Appl. Phys. Letts., Volume 67 (1995) 3918. In this device, polysilicon-based piezo-resistors are put on a cantilever and an integrated piezo-actuator. This device suffers from thermal and electrical noise issues. Low frequency noise is a very critical parameter. Significant noise problems make feedback tracking unstable and can result in crashing of the cantilever with the surface of the material being imaged.

BRIEF SUMMARY OF THE INVENTION

In accordance with the present invention, the disadvantages of prior sensors as discussed above have been overcome. The sensor of the present invention detects mechanical perturbations by a change in an electrical signal.

More particularly, the sensor includes a structure and a field effect transistor embedded in the structure wherein the transistor has an associated electrical current that changes with mechanical perturbations in the structure.

In another embodiment of the present invention, the sensor includes a first structure with a first field effect transistor embedded therein, the first structure having a surface coated with a material to which a probe molecule will adhere. The sensor also includes a second structure used as a reference with a second field effect transistor embedded in the second, i.e. reference, structure. The first and second field effect transistors are coupled to a differential amplifier to provide an electrical signal indicative of mechanical perturbations in the first structure caused by target molecules binding to probe molecules on the first structure.

In a further embodiment of the present invention, the sensor includes a structure and a field effect transistor embedded in the structure, the transistor providing an electrical signal that changes with mechanical perturbations in the structure. The sensor also includes a piezo-actuator on or embedded in the structure to provide bending and a feedback circuit that is coupled to the transistor and is responsive to the transistor's electrical signal to control the actuator.

These and other advantages and novel features of the present invention, as well as details of an illustrated embodiment thereof, will be more fully understood from the following description and drawings.

BRIEF DESCRIPTION OF THE SEVERAL VIEWS OF THE DRAWING

FIG. 9 is a perspective view of a sensor having a probe cantilever and a reference cantilever with probe and target molecules illustrated;

FIG. 11 is a graph illustrating drain current vs. drain voltage for different ODT concentration;

FIG. 12 is a graph illustrating the change in drain current vs. drain voltage for ODT detection;

DETAILED DESCRIPTION OF THE INVENTION

Figure 1:
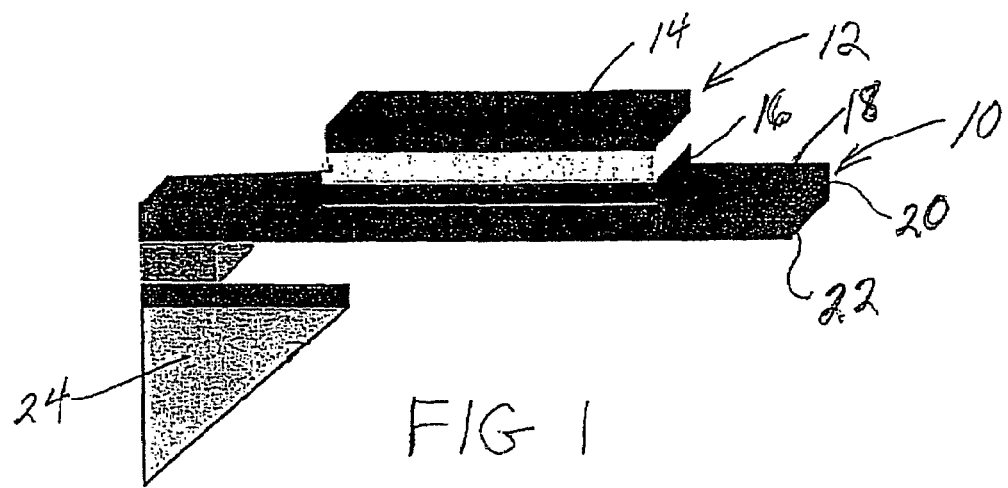
FIG. 1 is an illustration of an integrated actuator in the form of a BiMOS transistor on a cantilever for use in a nanosensor in accordance with the present invention.

The present invention relates to a novel sensor system based on silicon chip technology for electronic detection of molecular interactions. The present invention has ultra-high sensitivity, extremely low noise density and a cost effective technology platform and provides a powerful and easy to handle biological and chemical nanosensor for molecular and dangerous threat agent detection at ppb or ppq scale.

In accordance with one feature of the present invention, the sensing element is an integrated MOSFET (Metal Oxide Semiconductor Field Effect Transistor) transistor combined with a bipolar transistor, where the sensing element is placed at a high stress region of the micro-cantilever. The combined circuit of MOSFET and bipolar transistors is called BiMOS. The BiMOS platform not only has improved sensitivity, but also has an almost negligible noise figure (large signal to noise ratio), and ease of integration with CMOS and RF components. The micro-cantilever is immobilized with antibodies or a chemical sensitive layer. Upon interaction with threat agents, the cantilever bends due to either compressive or tensile stress resulting in a change in the drain current of the MOSFET chip. The bipolar transistor converts current to a voltage and amplifies the signal so as to eliminate the need for further functions in the amplification circuits. Multi-arrays with an integrated BiMOS chip embedded in them can act as a fingerprint for detection of toxic agents.

In accordance with another feature, the present invention relates to an integrated electric piezo-actuator and BiMOS electronic detector on the cantilever chip. The BiMOS output signal acts as a feedback signal to keep a constant separation between the cantilever and the surface of the material being imaged, thereby eliminating the need for optical detection of cantilever deflection. This feature will allow multi-parallel operation of the Scanning Probe Microscope which is not possible with current optical detection method.

Advantages of the present invention include (1) ease of integration with Si chip technology; (2) robust and highly sensitive detection; (3) cost-effective chip technology; (4) miniature size; (5) multi-analyte detection using a single platform; (6) arrayed readout with high sensitivity and ultra low noise density; (7) common mode rejection for noise cancellation; (8) wide dynamic range and easily integrated RF circuits; (9) low power electronics, power management circuitry and electrical self testing; and (10) single step label free assay, i.e. there is no need for fluorescent or radioactive labels, which reduces the amount of reagents required as well as the time for each reaction.

More particularly, in accordance with one feature of the present invention, sensing elements for biological and chemical agents use an array of micro-cantilever(s) with on-chip fabricated BiMOS electronic readout fabricated using CMOS technology. BiMOS readouts provides ultra-high sensitive detection of biomolecular and chemical interactions on the cantilever surface with very low noise density and ease of integration with microelectronics platform. Multiple arrays of such micro cantilevers will have potential applications for on-chip electronic noise. In accordance with another feature of the present invention, the cantilever comprises two sections: an actuator section, which includes an actuator that is located relatively near the fixed base of the cantilever; and a bending section, which is associated with a deflection detector and is located relatively near the free end (tip) of the cantilever. The actuator controls the position of the tip relative to the sample. The detector is a BiMOS electronic reader that detects the deflection of the cantilever. More particularly, the detector is a BiMOS readout, which provides a noise free feedback signal to maintain the cantilever at a constant distance from the surface of the material being imaged. Low noise feedback is of extreme importance in properly tracking the surface of the sample and measuring nm scale deflection of probes. This may help open completely new vistas in fabricating high frequency multi-active probes for developing high speed scanning probe microscopy imaging, patterning and analysis paradigm. Integrated piezoactuators will provide the necessary actuation of cantilever and drive it in resonance. It will provide the high speed AC mode detection of surface features.

The sensing element of the present invention as shown in FIG. 1 includes a micro-cantilever 10 with an integrated piezo-actuator 12. A BiMOS transistor is formed on or embedded in the micro-cantilever 10 as discussed below. These sensing elements may be used as Scanning Probe Microscopy Probes. The piezo-actuator 12 includes ZnO piezos having metallic contacts 14 and 16. The contact 16 is placed on a silicon dioxide layer 18 of the cantilever 10. The cantilever 10 also has a silicon nitride layer 20 and a second silicon dioxide layer 22. A probe 24 also includes a silicon dioxide layer 26.

Surface processes such as molecular adsorption/desorption can induce a stress, either tensile or compressive. In both cases, if the stress changes only on one side of a thin-cantilevered beam, the beam will permanently bend. The cantilever can therefore transduce a molecular/biomolecular adsorption at a single cantilever surface into a measurable mechanical deflection. The relationship between single-sided surface stress change, $\Delta\sigma$, and the resulting change in static deflection, $\Delta z$, is related by the following equation:

$$\Delta z \cong \frac{3(1-v)}{E} \frac{L^2}{t^2} \Delta\sigma$$

Where L and t are cantilever length and thickness and E and v are the Young's modulus and Poisson's ration, respectively, of the cantilever material. Surface adsorption processes (e.g. molecular/biomolecular adsorption) can therefore be sensed by measuring cantilever deflection. For a given material, stress sensitivity is proportional to the square of the length to thickness ration $(L/t)^2$. However, cantilevers are affected by external mechanical noise, which is damped by a factor proportional to $(f_{ext}/f_0)^2$ where $f_{ext}$ is the noise frequency and $f_0$ is the fundamental mechanical resonance frequency of the system. For optimal performance this resonance should be as high as possible. In the case of a rectangular cantilever the resonance frequency is given by:

$$f_0 \alpha \sqrt{\frac{E}{P} \frac{t}{L^2}}.$$

In order to maximize the overall sensitivity of the cantilever to stress-induced deflection, it is necessary to optimize $(L/t)^2$ and $(t/L^2)$ simultaneously. Miniaturizing the cantilever dimension aids this process via the high Q-factors of micro-machined Si structures. Microfabrication technologies will allow fabricating micrometer-sized cantilevers with high length to thickness ratio in a reproducible and inexpensive fashion. The dynamic response to such cantilevers is also well understood. The resonance frequency shift of an apex-loaded cantilever is a well-defined function of the loading, m where $$m = \frac{K}{4n\pi}\left(\frac{1}{f^2} - \frac{1}{f_0^2}\right).$$

K is the spring constant, n is the geometry dependent correction factor and $f_0$ and $f_1$ are the resonance frequencies of the unloaded and loaded sensor, respectively. For K on the order of 1 N/m and $f_0$ on the order of 100 kHz, the theoretical resolvable mass loading is on the order of femtograms.

To properly account for these fundamental mechanical properties the performance of the multifunctional cantilever sensor can be modeled and simulated through a joint effort of SPICE®, ANSYS® and Intellisuite® finite element analysis (FEA) programs. Optimization of cantilever width, thickness and resonance frequencies can be carried out with these software packages. Specific cantilever designs are targeted to optimize stress localization at the base of the cantilever for subsequent measurement via a MOSFET detector integrated with bipolar transistor as discussed below. In addition, a resonance frequency analysis of various cantilever designs can be carried out to analyze and optimize effects of mass loading. The FEA simulations reduce the need to perform detailed experimental optimization of the device characteristics. The lengths of the cantilevers in simulations that have been performed ranged from 200 to 450 μm and the thickness of the cantilevers in the simulations ranged from 1.5 to 3.0 μm. It has been found that maximum stress is generated at the base of the cantilever. This area is referred to as the stress concentration region (SCR). These simulated results guide in the placement of the piezo-resistor or BiCMOS actuator on the cantilever at a maximum in the SCR.

Figure 2:
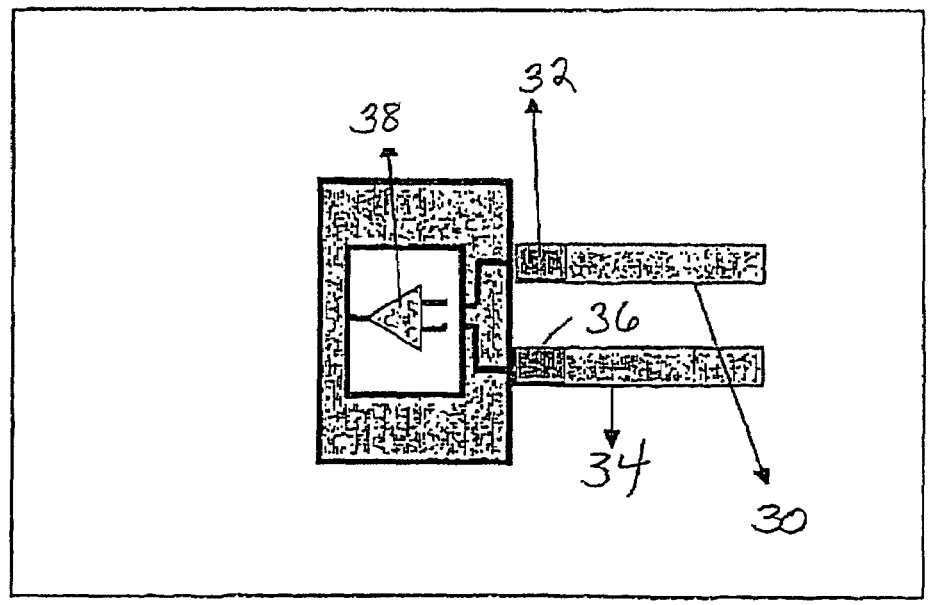
FIG. 2 is an illustration of an electrical schematic representing the integration of BiMOS electronic readout and actuator on cantilevers in a two cantilever configuration.

The electronic detection of bimolecular signals use a BiMOS electronic readouts integrated on micro-cantilever arrays. Built-in background filters are also integrated on the high stress region of the cantilever. Cantilever fabrication employs SOI wafers with buried oxide etch-stop layers, to provide probes with fully encapsulated BiCMOS resistors. The dimension of the resistors are defined and appropriate processes optimized to minimize leakage currents. Cantilevers with a force constant in the range of 1–5 N/m and with resonant frequencies in the range of 50–200 kHz are targeted for fabrication. The electronic configuration of the BiMOS chip is shown in FIG. 2. In this configuration, a Si sensor cantilever 30 has an integrated or embedded BiMOS reading or sensing element 32 that provides an electronic readout as described below. A Si reference cantilever 34 also has an integrated BiMOS transistor 36 as described below. Each of the BiMOS transistors 32 and 36 are coupled to a CMOS Differential Amplifier 38 to provide an output. The primary advantage of the present invention is the lower noise figure associated with a combination of a MOS and a bipolar (Bi-MOS) stress transistor as compared to wheatstone bridge configuration and the ease of integration with RF and BiCMOS components on a chip.

The drain-source current of the embedded BiMOS transistor is biased in the saturation region and can be easily modulated with mechanical stress in the conducting channel. See for example, D. Colman, R. T. Bate, J. P. Mize, Journal of Appl. Phys., Volume 39 (1968) 1923. The relative change in the source-drain current of a BiMOS transistor under stress is a function of the piezo-resistive coefficient $\pi$ of the inversion layer and the stress $\sigma$: $\Delta I_d/I_d = -\pi\sigma$. The size of the BIMOS stress transistor will be maximized to minimize 1/f noise. The advantage of using BiMOS is two folded. First, high current sensitivity of the MOS transistor will be utilized to detect molecular interactions in ppt or ppq scale. Secondly, high frequency bipolar transistors will convert the current into a voltage signal and amplify it to have further high fan out capability. In other words, as bipolar transistors are high power devices, they can further drive more electronic circuits on the chip. Moreover, bipolar transistors have minimal low frequency noise. The unique combination of a MOS and a bipolar transistor will provide a noise free detection of toxic ions.

Figure 3:
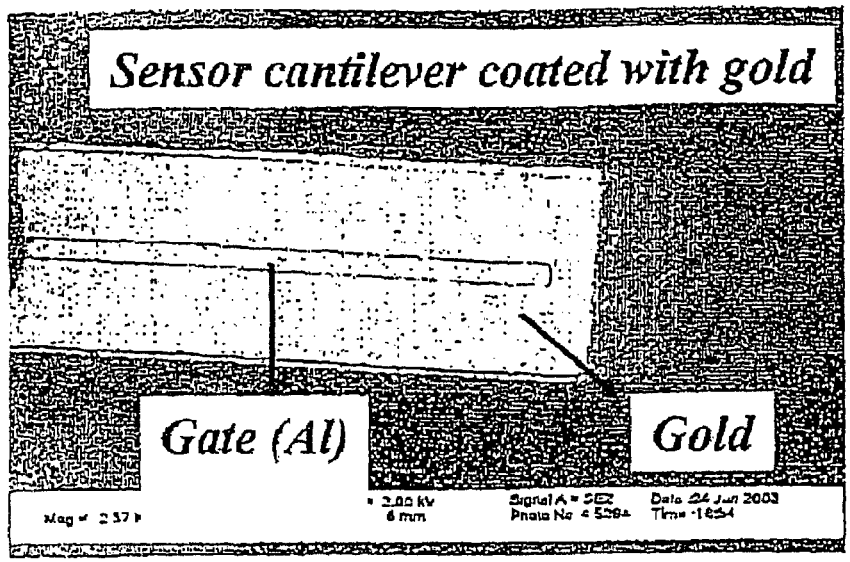
FIG. 3 is an illustration of a cantilever with an integrated BiMOS electronic read-out.
Figure 4:
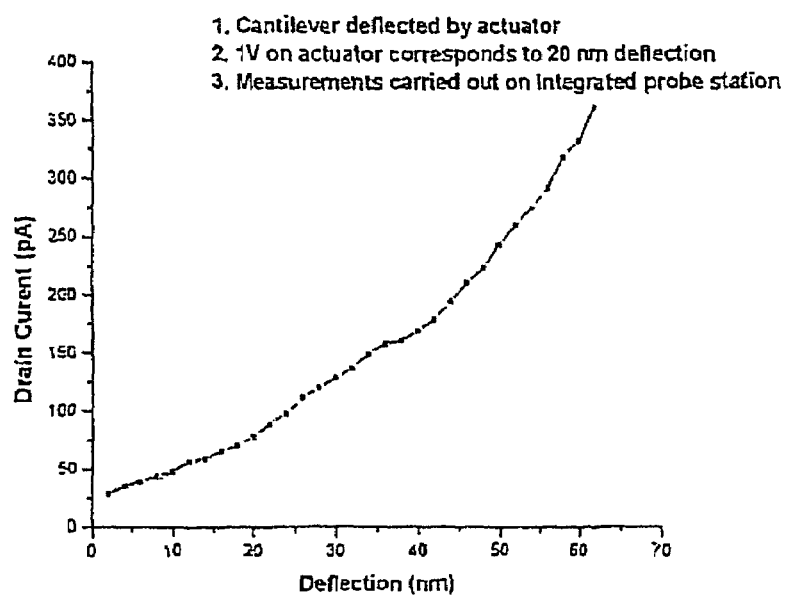
FIG. 4 is a graph of the current versus voltage characteristics of the BiMOS piezo-actuator after the cantilever is deflected.
Figure 5:
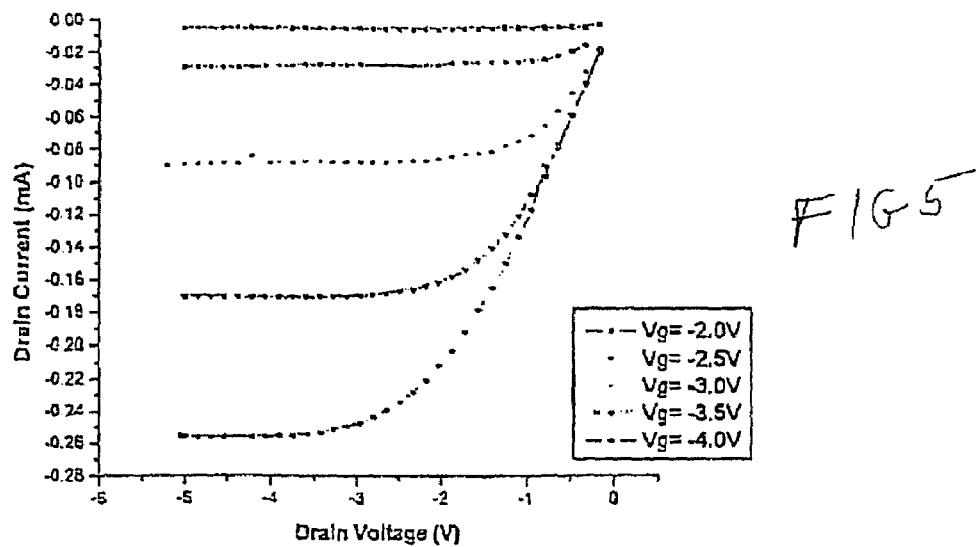
FIG. 5 is a graph of the normal characteristics of a MOSFET transistor.

A first proof of concept device was successfully fabricated. Initially, only embedded MOSFET readouts were put on the fabricated cantilever structures as shown in FIG. 3. These cantilevers were used in the two-cantilever configuration of FIG. 2 where one of the cantilevers is designated as reference and the other cantilever is designated as a sensor cantilever. Standard MEMS technology was used to fabricate these cantilevers. In this device geometry, MOS field effect transistors are formed on the high stress region of the cantilever. Electrical testing can be carried out using an integrated probe station in order to verify the performance characteristics of the embedded MOSFET electronic readouts. FIG. 4 shows the current vs. voltage plot for one of the MOSFET embedded in the cantilever. The actuator physically bent the cantilever. Initial results clearly indicate that the transports can detect 1 nm of cantilever deflection. Out current sensitivity, $\Delta I/I$, was approximately $10^{-6}$, which is quite close to that for optical detection. Electrical measurements were also carried out for testing the embedded MOSFET device and results are depicted in FIG. 5.

Figure 6:
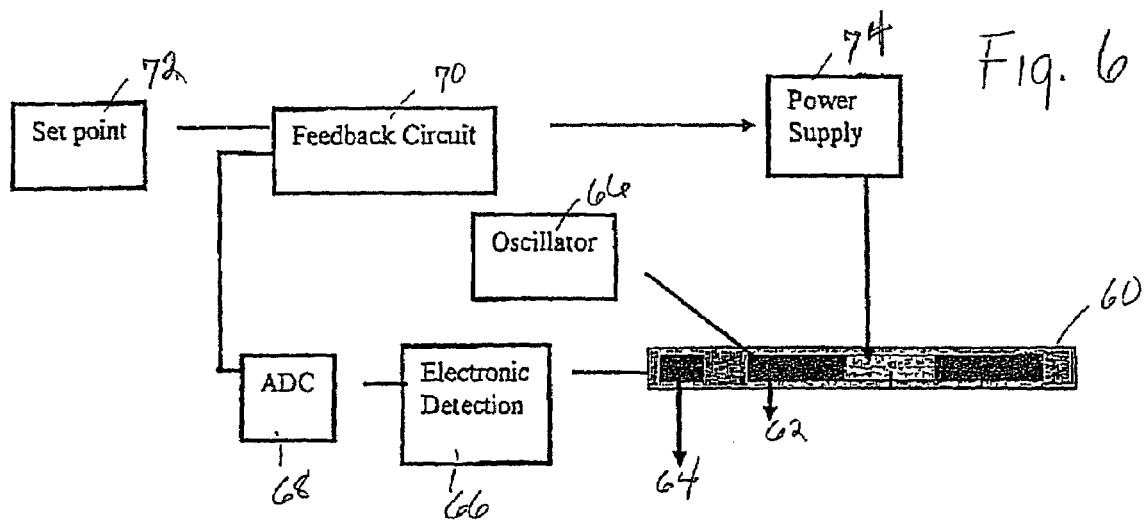
FIG. 6 is a block diagram of a feedback controlled integrated cantilever.

A noise free parallel Scanning Probe Microscope (SPM) using multi arrays of cantilevers with integrated highly sensitive BiMOS transistors for actuation and electrical detection of cantilever deflection is shown in FIG. 6. As shown therein, a Si cantilever 60 has an integrated piezo-actuator 62 and a BiMOS electronic readouts 64. An oscillator 66 is coupled to the actuator 62 to drive the actuator. The BiMOS readouts 64 is coupled to an electronic detection circuit 66, the output of which is coupled to an analog-to-digital converter 68. The output of the analog-to-digital converter 68 is coupled to a feedback circuit 70 to which a set point 72 is also coupled. The output of the feedback circuit is used to adjust the power supply voltage 74 applied to the Au contacts of the actuator 62. The electrical detection and feedback control will allow the SPM to have multiple arrays, which will scan a whole 100 mm wafer in a span of few seconds. High frequency integrated actuators will increase the speed of the scanning and individual control of each cantilevers in an array. The present invention may be used in parallel SPM for imaging surface structures, dip pen nanolithography and nanopatterning, where one can control physical dimensions of individual pattern.

Figure 7:
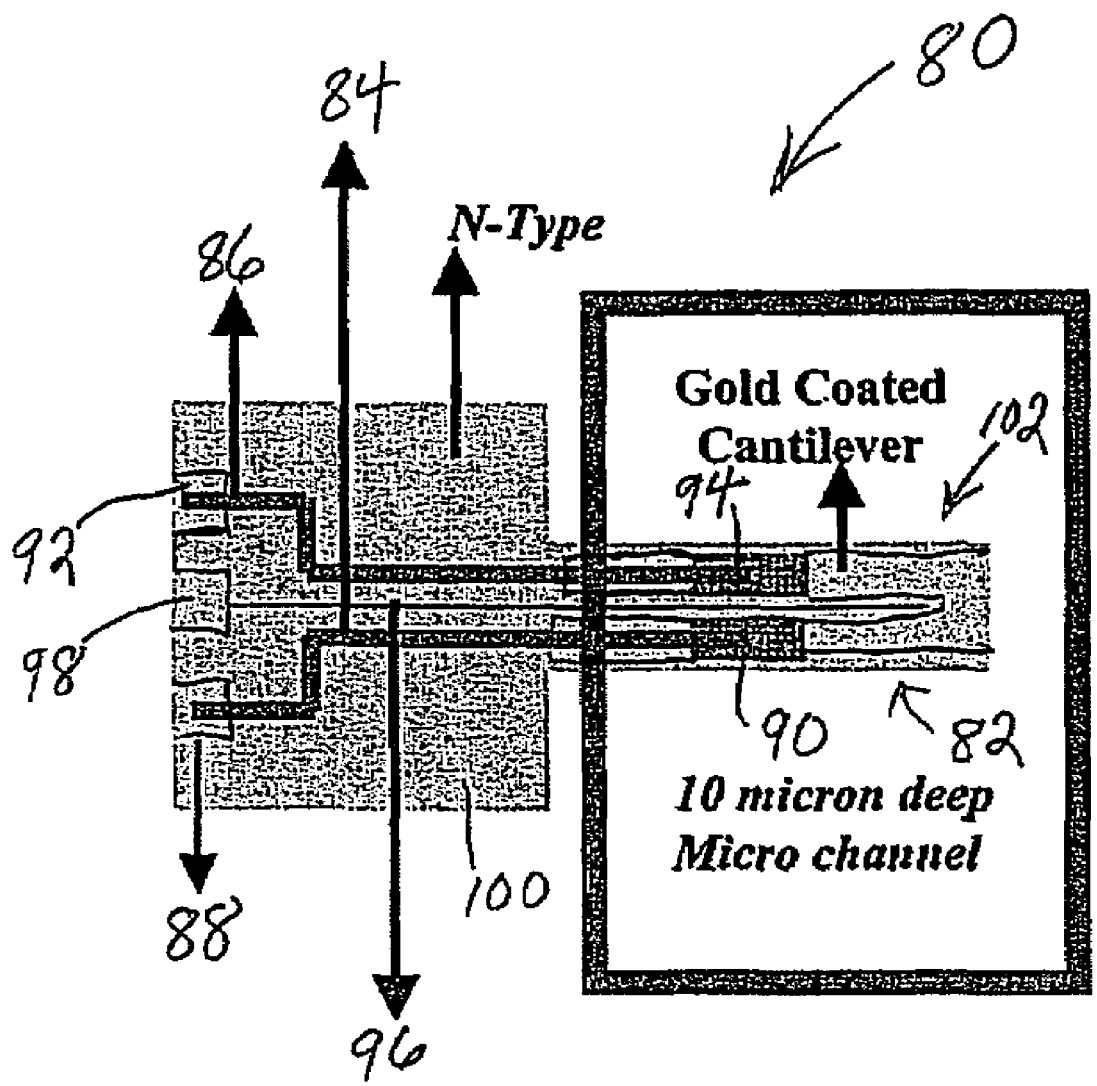
FIG. 7 is a top cross-sectional view of a MOSFET embedded microcantilever in accordance with one embodiment of the present invention.

FIG. 7 illustrates a sensor 80 for detecting mechanical perturbations in a structure, such as a cantilever 82, with a field effect transistor, that is preferably MOSFET embedded in the cantilever structure 82, such that the transistor provides an electrical signal or readout that changes with mechanical perturbations in the cantilever 82. Specifically, mechanical perturbations in the cantilever 82 result in a change in the drain current of the embedded BiMOS or MOSFET. For example, when the sensor 80 is used for bio-chemical sensing, the cantilever bends due to either compressive or tensile stresses caused by an interaction between target molecules and probe molecules on the cantilever as discussed below. Multi-arrays with integrated BiMOS chips embedded therein can act as a fingerprint for the detection of for example, toxic and biological agents. The embedded BiMOS is a means of detecting change in nanomechanics, e.g. bending, vibrations etc., and can be applied not only to microcantilevers but to other structures which require a detection scheme for mechanical stress or deflection such as cantilever arrays, membranes, MEMS devices, etc. Moreover, the sensor is not limited to conventional Si transistors as discussed below. The invention also applies to other forms of field effect transistors, including polymer/organic, SiC/GaN, nanotube, etc., types of field effect transistors.

The structure shown in FIG. 7 is a NMOS structure wherein the embedded MOSFET has a N+ drain contact formed of Al 84 and a N+ source contact 86 similarly formed of Al. The N+ drain contact 84 extends from a gold, i.e. Au, contact 88 to a P-type drain 90. The N+ source contact extends from a gold contact 92 to a P-type source 94 on the cantilever 82. The gate 96 of the MOSFET shown in FIG. 7 is formed of an Al contact that extends from a gold contact 98 on the silicon base 100 to a free end 102 of the cantilever 82. The layer by layer details of the sensor 80 of FIG. 7 are as follows. First, a three micron epi Si layer forms a base of the sensor. Next, a 100 nm oxide layer is formed on the Si layer. Thereafter, the P-type source and drain regions 94 and 90 are formed in a third layer. The fourth layer includes the Al contacts for the source 86 and the drain 84. The fifth layer includes a 20 nm gate oxide and the sixth layer includes 100 nm SiN layer. In a seventh layer, the Al contact 96 for the gate of the MOSFET is formed. The eighth or top layer is formed by a gold or Au coating on the whole cantilever or with the exception of the Al contact for the gate when the structure is used as a probe structure as discussed below. Although a NMOS sensor is shown in FIG. 7, by changing the doping, a PMOS sensor can be formed. A PMOS structure creates less flicker noise due to low mobility and a large gate area in order to suppress 1/f noise.

Figure 8A:
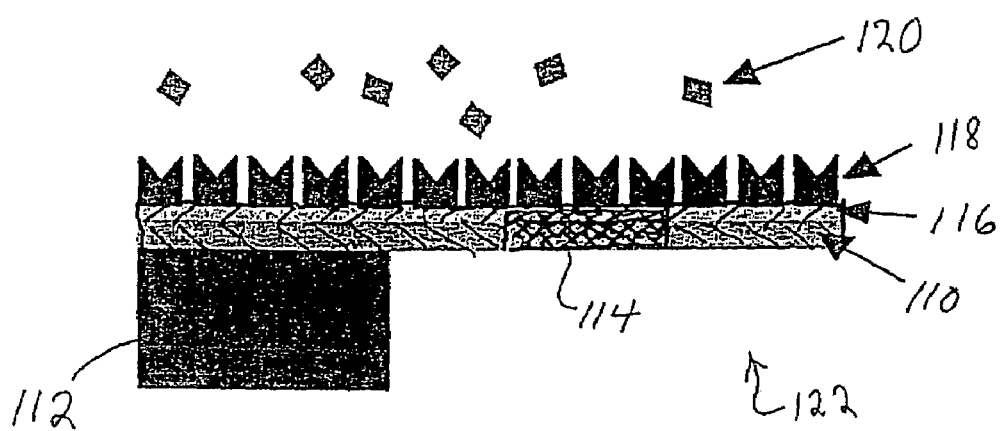
FIGS. 8A–B is a side cross-sectional view of a MOSFET embedded microcantilever with probe molecules and target molecules illustrated.
Figure 8B:
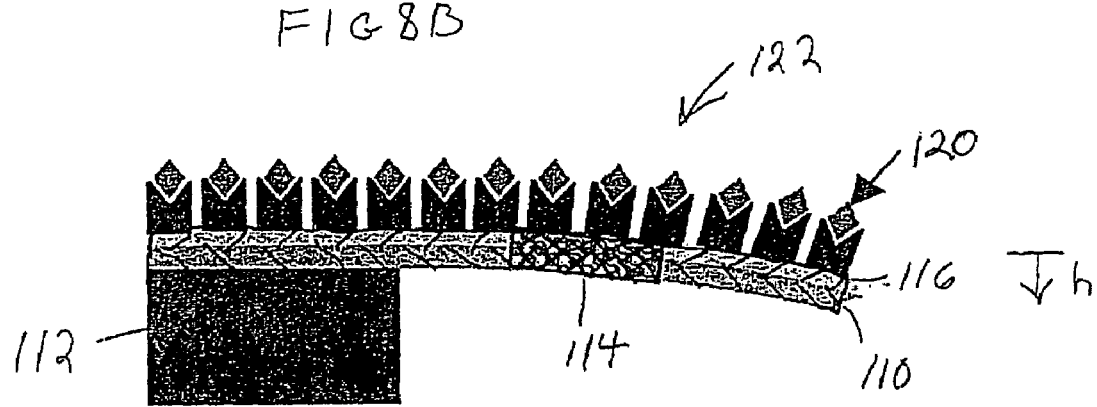

Cross-sectional views of a MOSFET embedded microcantilever for detecting biomolecular interactions are shown in FIGS. 8A and 8B. The cantilever 110 is a silicon nitride microcantilever with an embedded MOSFET 114 as described above. The microcantilever 110 is supported on a silicon base 112 and has a coating 116 of gold on a surface of the microcantilever 110. In order to use the sensor 122 to detect a toxic agent, for example, the sensor 122 is dipped in a solution of probe molecules 118 where the probe molecules are antibodies of the toxic agent that is being tested for. Thereafter, the sensor 122 is dipped in a solution of the target molecules 120 that are being tested for. If the target molecules 120 bind to the probe molecules 118, stress is induced in the cantilever 110 causing the cantilever to bend either up or down as shown in FIG. 8B indicating that the toxic agent being tested for is present in the target solution. The relationship between single-sided surface stress change, $\sigma$, and the resulting change in static deflection, $\sigma Z$, is related by the following equation as discussed above.

$$\Delta z \cong \frac{3(1-v)}{E} \frac{L^2}{t^2} \Delta \sigma$$

The change in $\sigma$ induces a change in the drain current $i_d$ of the embedded MOSFET 114 so as to provide an electrical signal and electrical readout representing the mechanical perturbations in the cantilever 110 caused by target-probe binding. In this example, the deflection of the cantilever indicates the presence of the target molecule in the solution being tested.

Figure 10:
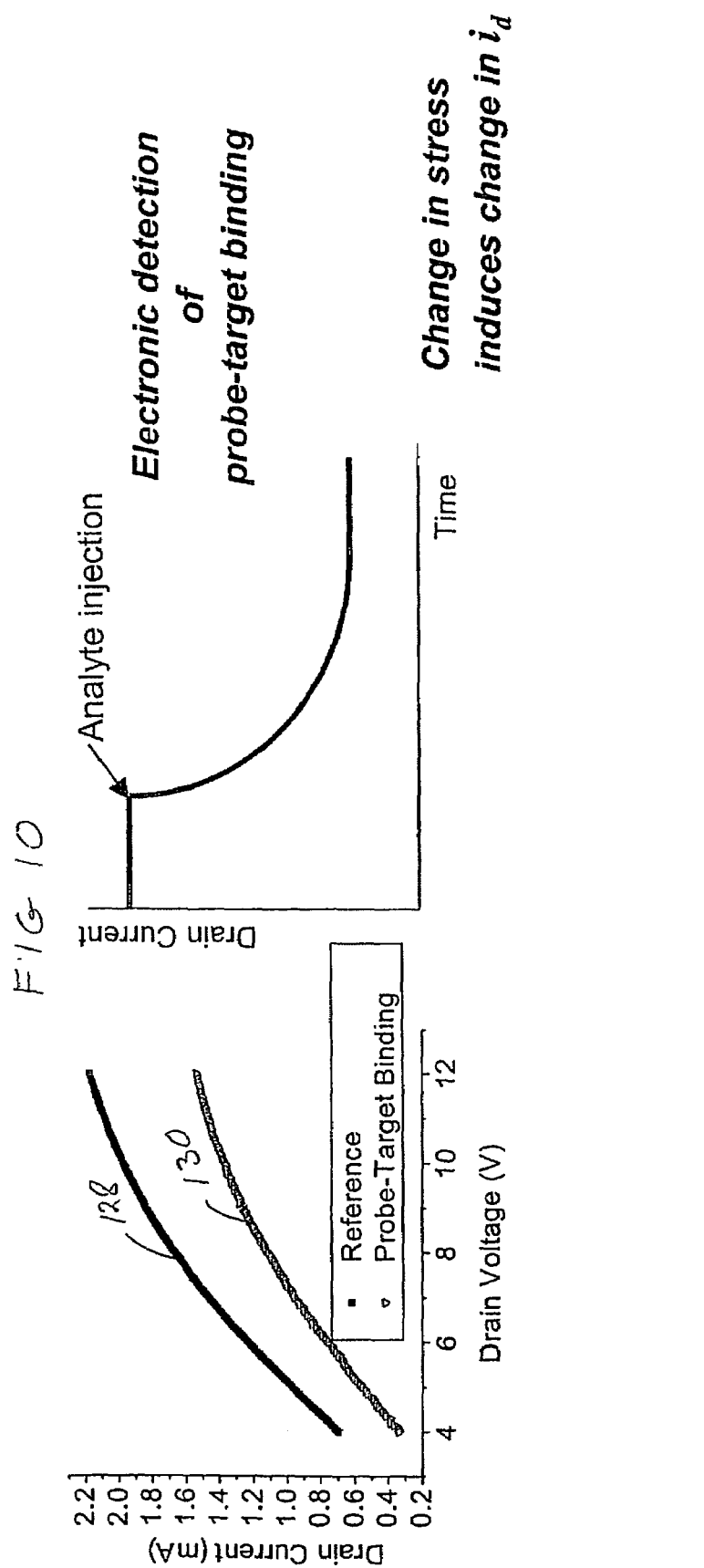
FIG. 10 is a graph illustrating drain current vs. voltage and time for the sensor of FIG. 9.

As shown in FIG. 9, the sensor 124 includes a probe microcantilever 110 with embedded MOSFET 114 as discussed above with reference to FIGS. 8A–B. The sensor 124 also includes a reference cantilever 126 with an embedded MOSFET 116. Both of the cantilevers 110 and 126 are formed of silicon nitride with the various layers described above with reference to FIG. 7. However, the cantilevers differ in that the probe cantilever 110 has the gold or Au coating whereas the reference cantilever 126 does not have the gold coating. Because the reference cantilever 126 does not have the gold coating, when the sensor 124 is dipped in a solution of probe molecules 118, the probe molecules do not adhere to the reference cantilever 126 but will adhere to the probe cantilever 110. Thereafter, when the sensor 124 is dipped in the solution to be tested, if the target molecules are present, the target molecules will bind to the probe molecules on the probe cantilever 110, but the target molecules will generally not bind to the reference cantilever 126. In this embodiment, each of the transistors 114 and 116 is coupled to a CMOS differential amplifier as discussed above to provide an electronic readout that represents the difference in the induced stress in the cantilevers 110 and 126. The reference cantilever 126 is used to nullify bending of the cantilevers 110, 126 that results from other than the target molecules being tested for. FIG. 10 illustrates the drain current vs. drain voltage and drain current vs. time for the electronic detection of probe target binding as discussed above with reference to FIG. 9. More particularly, the graphs 128 represents the drain current vs. drain voltage for the reference transistor 116 whereas the graph 130 represents the drain current vs. drain voltage for the transistor 114 with probe target binding.

Figure 14:
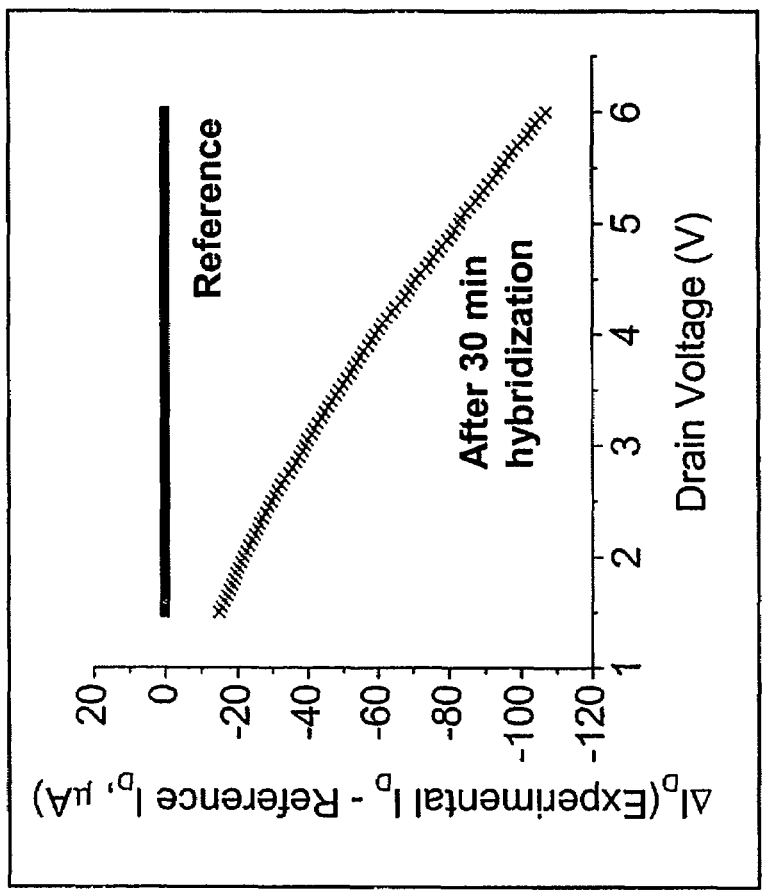
FIG. 14 is a graph illustrating the change in drain current vs. drain voltage for the electronic detection of DNA hybridization.
Figure 13:
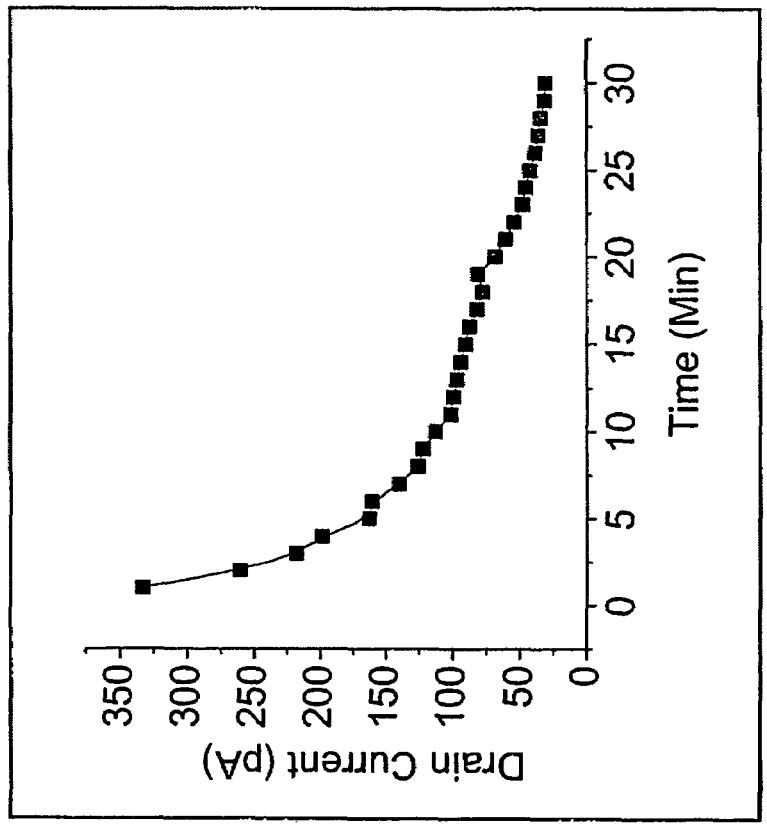
FIG. 13 is a graph illustrating drain current vs. time for the electronic detection of DNA hybridization.
Figure 16:
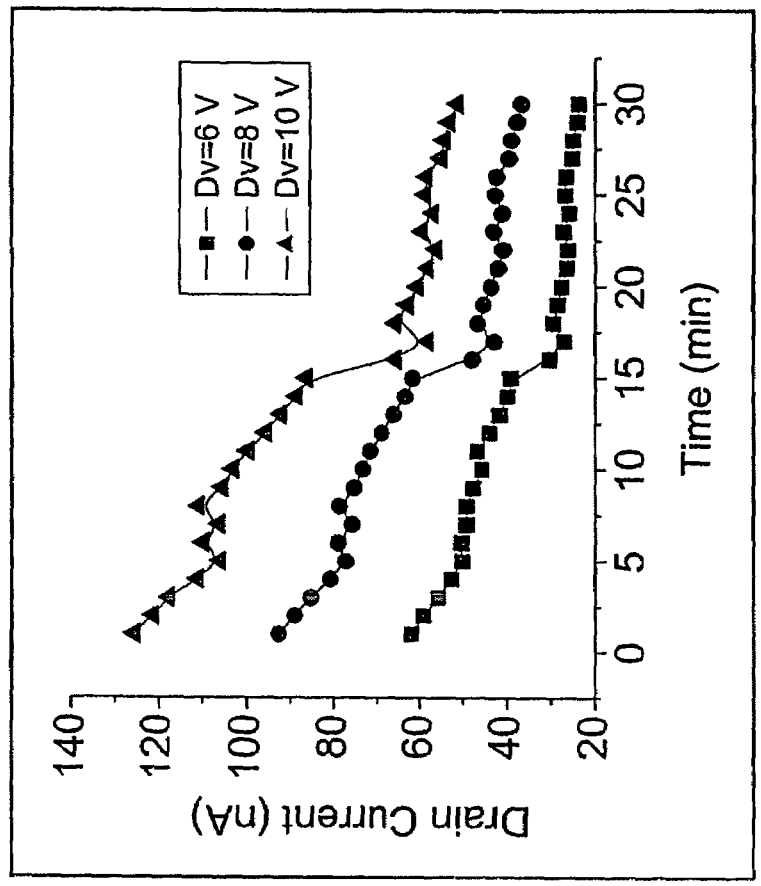
FIG. 16 is a graph illustrating drain current vs. time for streptavidin and 50 nM biotin binding at Gv=1.0V and three different drain voltages.
Figure 15:
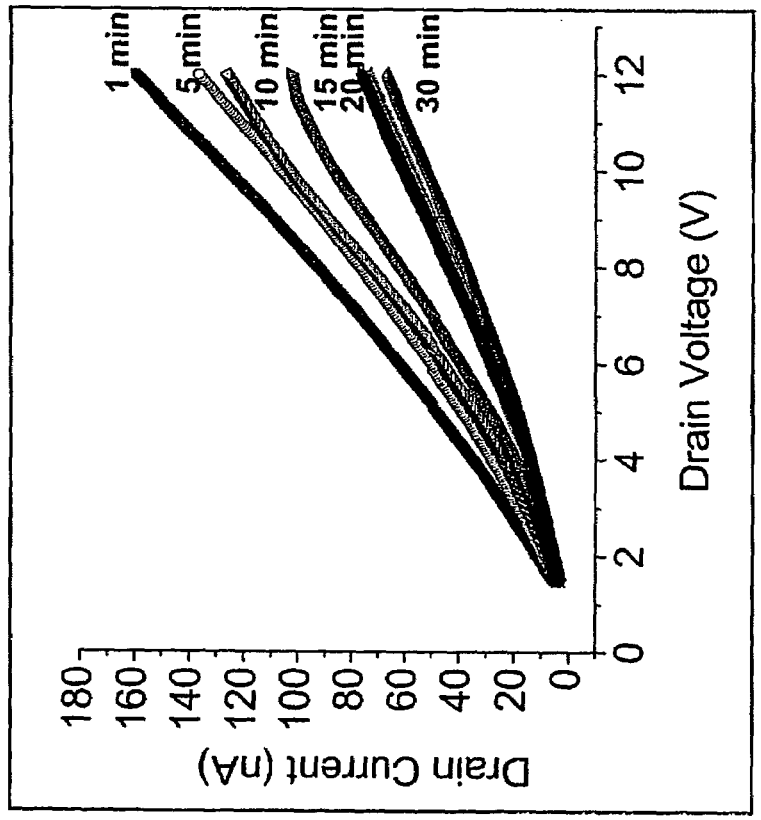
FIG. 15 is a graph illustrating time dependent drain current vs. drain voltage measurement for streptavidin and 50 nM biotin binding at Gv=1.0V.
Figure 18:
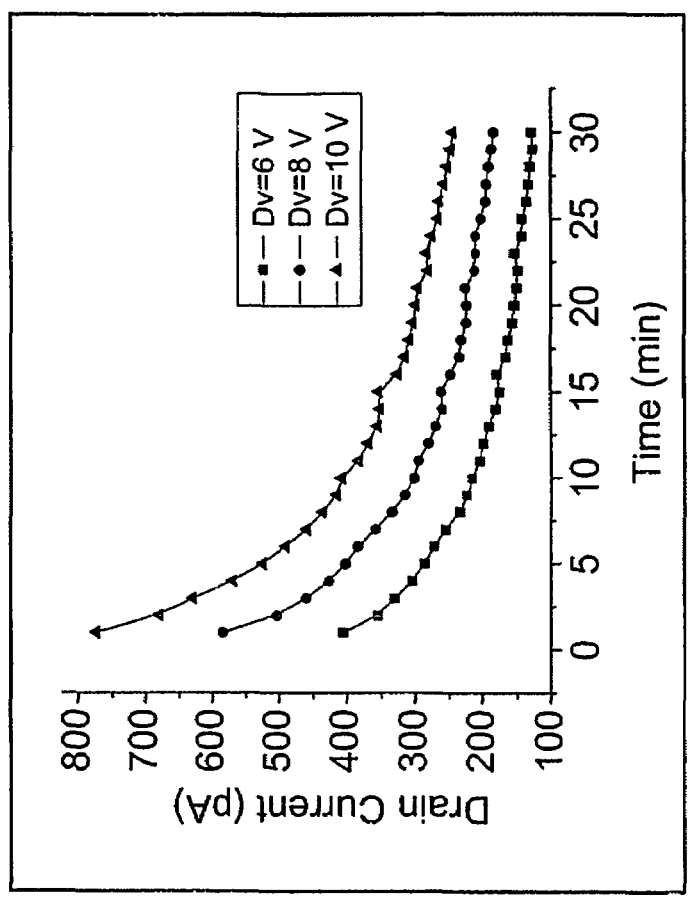
FIG. 18 is a graph illustrating drain current v. time for three different drain voltages for the electronic detection of Atrazine Antigen-antibody binding.
Figure 17:
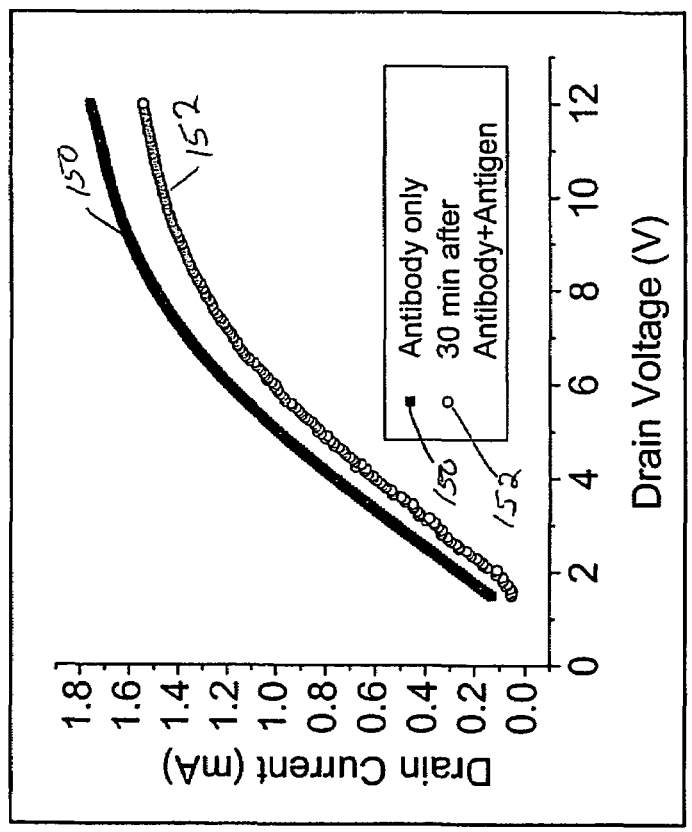
FIG. 17 is a graph illustrating drain current vs. drain voltage at Gv=1.0V for the electronic detection of Atrazine Antigen-antibody binding.

FIGS. 11 and 12 illustrate ODT detection using a MOSFET embedded cantilever sensor as discussed above. More particularly, FIG. 11 illustrates the drain current vs. drain voltage for different ODT concentrations at Gv=1.5V. FIG. 12 illustrates the change in drain current vs. drain voltage at Gv=1.0V. The graph 136 represents no ODT; the graph 137 illustrates 10 mM ODT; the graph 138 illustrates 30 mM ODT and the graph 139 illustrates 50 mM ODT. In FIG. 12, the graph 140 represents bare gold, the graph 142 represents 40 mM ODT and the graph 144 represents SiN with ODT. FIGS. 13 and 14 depict electronic detection of DNA hybridization. Specifically, FIG. 13 depicts the drain current vs. time for 40 nM target ssDNA hybridization at Gv=1.0V and Dv=6.0V. As shown, drain current decreases with hybridization time and reaches saturation in approximately 30 minutes. FIG. 14 shows the change in drain current vs. drain voltage at Gv=1.0V for 40 nM target ssDNA. FIGS. 15 and 16 illustrate electronic detection of streptavidin-biotin binding. Specifically, FIG. 15 depicts the time dependent drain current vs. drain voltage measurement for streptavidin and 50 nM biotin binding at Gv=1.0V. FIG. 16 illustrates the drain current vs. time for streptavidin and 50 nM biotin binding at Gv=1.0V and three different drain voltages. FIGS. 17 and 18 illustrate the electronic detection of Atrazine Antigen-antibody binding. More particularly, FIG. 17 illustrates the drain current vs. drain voltage at Gv=1.0V for an antibody only 150 and at 30 minutes after the antigen-antibody binding at 152. As can be seen, drain current decreases with antigen (0.1 mg/ml) antibody (0.1 mg/ml) binding. FIG. 18 depicts drain current vs. time for three different drain voltages.

Many modifications and variations of the present invention are possible in light of the above teachings. Thus, it is to be understood that, within the scope of the appended claims, the invention may be practiced otherwise than as described hereinabove.

The invention claimed is:

1. A sensor for detecting mechanical perturbations represented by a change in an electrical signal comprising:
    a cantilever structure;
    a BiMOS embedded in the cantilever structure, the BiMOS including a metal-oxide semiconductor field effect transistor measuring deflection of the cantilever and a bipolar transistor providing an amplified signal;
    a piezo-actuator on or embedded in the cantilever structure to provide bending of the cantilever structure; and
    a feedback circuit responsive to the signal from the BiMOS to control the piezo-actuator.

2. A sensor for detecting mechanical perturbations represented by a change in an electrical signal as recited in claim 1 wherein said cantilever is an Si cantilever.

3. A sensor for detecting mechanical perturbations represented by a change in an electrical signal as recited in claim 2 wherein the feedback circuit is responsive to the transistor's electrical signal to adjust a voltage applied to the piezo-actuator.

* * * * *